US006841518B2

(12) United States Patent
Malavenda

(10) Patent No.: US 6,841,518 B2
(45) Date of Patent: Jan. 11, 2005

(54) METHOD FOR CONTROLLING ROOT GROWTH USING PARAQUAT

(75) Inventor: Anthony John Malavenda, Dewitt, NY (US)

(73) Assignee: Egoutech LLC, Syracuse, NY (US)

( * ) Notice: Subject to any disclaimer, the term of this patent is extended or adjusted under 35 U.S.C. 154(b) by 0 days.

(21) Appl. No.: 10/322,300

(22) Filed: Dec. 18, 2002

(65) Prior Publication Data

US 2004/0121912 A1 Jun. 24, 2004

(51) Int. Cl.[7] .......................... A01N 25/16; A01N 43/40
(52) U.S. Cl. ..................................... 504/250; 504/363
(58) Field of Search .................................. 504/250, 363

(56) References Cited

U.S. PATENT DOCUMENTS

| | | | | |
|---|---|---|---|---|
| 4,171,967 A | * | 10/1979 | Parham et al. .................. | 71/74 |
| 4,764,206 A | * | 8/1988 | Yamashita et al. .......... | 504/250 |
| 5,116,414 A | * | 5/1992 | Burton et al. .................. | 71/121 |
| 5,919,731 A | | 7/1999 | Malavenda et al. ......... | 504/136 |

OTHER PUBLICATIONS

Saeed et al., "Acute diquat poisoning with intracerebral bleeding, " 2001, Postgrad. Med. 77(907):329–332.
Syngenta Gramoxone® Max product literature, printed 2001.
Groninger and Bohanek, "Effects of Diquat applied to exposed roots of Black Willow," 2000, J. of Plant Growth Regulation 19:453–456.
Lam et al., "A comparison of the effects of paraquat and diquat on lung compliance, lung volumes and single breath diffusing capacity in the rat," Toxicol. 18:111–123.
Vanholder et al., "Diquat Intoxication: Report of two cases and reciew of the literature, " 1981, Am. J. Med. 70:1267–1271.
Bismuth et al., "Prognosis and treatment of paraquat poisoning:A review of 28 cases," 1982, J. Toxicol. Clin. Toxicol. 19:461–474.

* cited by examiner

Primary Examiner—S. Mark Clardy
(74) Attorney, Agent, or Firm—Baker Botts L.L.P.

(57) ABSTRACT

The present invention relates to the use of paraquat as a root control agent. It is based, at least in part, on the results of green house testing in which application of paraquat ion as a dense foam to tree roots resulted in the destruction of the test roots without causing damage to the upper portion of the trees. The inactivation of paraquat by organic materials, under these circumstances, becomes an advantage, as it prevents toxic levels of paraquat from traveling downstream from the point of application 21 Claims, 4 Drawing Sheets

METHOD FOR CONTROLLING ROOT GROWTH USING PARAQUAT

The present invention relates to a method for controlling root growth comprising applying, to exposed plant roots, an effective amount of paraquat ion. It is based, at least in part, on the discovery that paraquat ion, a herbicide previously used primarily to destroy plant tissue by blocking photosynthesis, is also toxic to root tissue when locally applied. Such methods are particularly useful in reducing the amount of roots present in sewer pipes.

BACKGROUND OF THE INVENTION

A number of chemical products have hitherto been used to control vegetative root intrusion in pipeline systems. The most frequently used active ingredients in such products are copper sulfate, corrosive acids or bases, 2,6 dichlorobenzonitrile (hereafter "Dichlobenil") and sodium methyldithiocarbamate (hereafter "Metam"). Each of these products, however, suffer from a number of disadvantages which render their use problematic.

For example, copper sulfate is not detoxified by wastewater treatment plants and, because it is a systemic herbicide, can damage above-ground vegetation. Corrosive acids and bases, such as sulfuric acid, hydrochloric acid, caustic soda, and sulfamic acid, use heat as the primary mechanism of root destruction, and as such are effective only at the point of application and do little to prevent regrowth. Dichlobenil acts upon growth points in root systems and therefore provides residual control by deterring regrowth, but has limited effectiveness, so that it is commonly formulated with the active agent Metam. Combinations of Metam and Dichlobenil were found to be so effective, they replaced other types of active ingredients in the industry. However, several problems associated with Metam were identified which created a motivation to find other suitable herbicides for root control. First, Metam is a carcinogen. Second, in concentrations typically used for root control, Metam may be toxic to microorganisms at biological wastewater treatment plants, where it may be particularly toxic to nitrifying bacteria. Third, Metam is a marine pollutant, and therefore is not amenable to storm drain applications unless costly precautions are taken to ensure against a release of Metam into fresh water sources such as streams, ponds and lakes.

U.S. Pat. No. 5,919,731 discloses the use of diquat as an effective agent against root growth in sewer pipes. Previously, diquat had been known as an herbicide which killed foliage by photosynthesis, and which was inactivated by organic materials. The mechanism by which diquat kills roots in sewers, where there is little or no photosynthesis occurring, and where there is an abundance of organic material, has not been determined. Although toxicity has been postulated to be associated with diquat's desiccant activity, this has not been confirmed. Toxicity issues associated with Metam are obviated by using diquat as a root control agent, because diquat's toxicity is limited due to its inactivation by organic matter.

Paraquat is chemically related to diquat, both being dipyridyl compounds. It is known in the art to share some, but not all, of the biological activities of diquat. For example, paraquat, like diquat, is an herbicide which acts by inhibiting photosynthesis and is inactivated by organic substances. However, the toxicology of paraquat and diquat are different. In animals, the primary target for paraquat toxicity is the lungs (Bismuth et al., 1982, J. Toxicol. Clin. Toxicol. 19:461–474), whereas diquat is severely toxic to the nervous system and does not produce significant pulmonary damage (Saeed et al., 2001, Postgrad. Med. 77(907):329–332; Lam et al., 1980, Toxicol. 18:111–123; Vanholder et al., 1981, Am. J. Med. 70:1267–1271).

Because the herbicidal mechanism shared by diquat and paraquat is not believed to operate in root control, it was not known, prior to the present invention, whether paraquat would be an effective root control agent. The fact that the primary toxic effects of diquat and paraquat in animals involve different organ systems contributed to this uncertainty, because it suggests that some tissues susceptible to damage by diquat are resistant to paraquat toxicity.

SUMMARY OF THE INVENTION

The present invention relates to the use of paraquat and its derivatives as root control agents. It is based, at least in part, on the results of green house testing in which application of paraquat as a dense foam to tree roots resulted in the destruction of the test roots without causing damage to the upper portion of the trees.

In a first set of embodiments of the invention, paraquat is applied to exposed roots as a foam comprising paraquat, where paraquat may be the sole root control agent or may be combined with additional root control agents, including, but not limited to, diquat and/or Dichlobenil.

In a second set of embodiments, paraquat may be applied, as the sole root control agent or combined with one or more additional root control agent, to exposed roots as a spray. In specific, non-limiting embodiments, the spray may be administered via a hydraulic sewer cleaning machine (commercially known as a "Sewer Jet" or "Hydraulic Sewer Cleaning Machine). Such an apparatus pumps water through a hose at high pressure through a nozzle having ports facing rearwards, thereby propelling the Sewer Jet hose down a pipeline, while flushing debris from the pipe.

Accordingly, the present invention provides for methods and compositions for using paraquat as a root control agent. This root control activity may be used to reduce, relieve and or/inhibit obstruction of conduits such as sewers, or in other contexts where roots enter an open space.

DETAILED DESCRIPTION OF THE INVENTION

Figure 1:
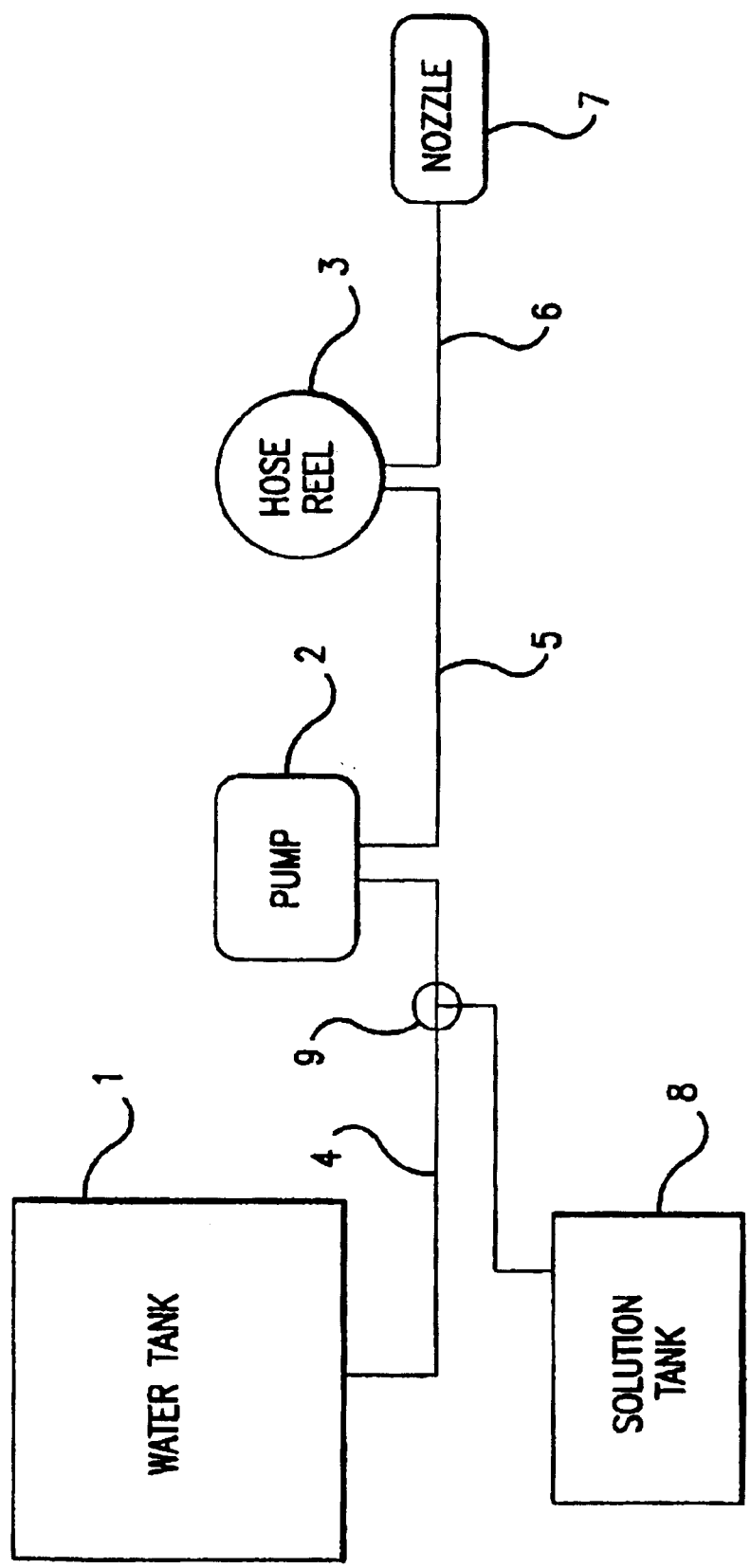
FIG. 1. Schematic diagram of Sewer Jet, wherein a water storage tank (1) is linked to a high pressure pump (2) via a suction line (4), and the high pressure pump is able to pump water through a pressure line (5) to a hose reel (3) connected to a high pressure hydraulic sewer cleaner hose (6) having a jet nozzle (7). A solution of root control agent is introduced into the system from a holding tank (8) connected to the suction line (4) via a three-way valve (9).

The present invention provides for compositions and methods for destroying plant root tissue, comprising applying, to the tissue, an effective amount of paraquat ion, the technical name of which is 1,1'-dimethyl-4,4'-bipyridium ion, and which has the chemical structure:

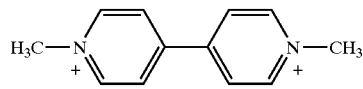

(the term "paraquat" as used herein refers to the ion). Paraquat is typically provided as 1,1'-dimethyl-4,4'-bipyridium dichloride, for example, and not by way of limitation, as sold by Syngenta Inc., under the commercial name Gramoxone Max® as 43.8 percent paraquat and 56.2 percent inert ingredients wherein 3 pounds of paraquat ion per gallon are found in a solution having 4.143 pounds of the dichloride salt per gallon.

According to the invention, a composition comprising an effective amount of paraquat may be applied to a root to control the growth of the root. Growth control may be achieved by destruction of all or a portion of the root tissue. Preferably, after an effective amount of paraquat is applied to a root mass, the amount of living root present decreases by at least 75 percent within a period of 25 days. Preferably, an effective amount of paraquat is toxic within 25 days when applied to a root which is 3 mm in diameter.

Paraquat may be applied, according to the invention, as a solution for application by either pressure spray or foam, or any other method known in the art. In specific non-limiting embodiments of the invention, the solution comprises between 0.00219 and 0.876 percent paraquat, preferably between 0.00438 and 0.438 percent paraquat, and more preferably between 0.0219 and 0.219 percent paraquat. Paraquat solutions may be prepared, in nonlimiting examples of the invention, by diluting between 0.005 to 2.0 gallons of paraquat stock aqueous solution (e.g., Gramoxone Max®, having a concentration of 43.8 percent per gallon, referred to herein as a paraquat stock solution, and intended for further dilution prior to application) per 100 gallons of mixed solution; preferably by diluting between 0.01 to 1.0 gallons of the foregoing paraquat stock solution (43.8 percent) per 100 gallons of mixed solution; and more preferably by diluting 0.05 to 0.5 gallons of paraquat stock solution (43.8 percent) per 100 gallons of mixed solution.

Such solutions, comprising paraquat, may further comprise other agents, such as diquat, Dichlobenil, Metam and/or ammonium sulfate, at effective concentrations. In a specific, non-limiting embodiment, a solution may be prepared comprising paraquat at a concentration of between about 0.0438 and 0.876 percent and diquat at a concentration of between about 0.0373 and 0.746 percent.

Such solutions may also comprise adjuvants which act as carriers, facilitate the removal of organic substances, improve the ability of the active ingredients to adhere or penetrate root tissue, or otherwise improve the efficacy of the treatment, including, but not limited to, detergents, degreasers, emulsifiers, foaming agents, surfactants, wetting agents, penetrants, spreaders, and sticking agents.

In a first set of embodiments, paraquat solution may be applied to exposed roots as a foam, using standard equipment. The most common method of foaming herbicides in sewers, is to mix the herbicide in solution with water and foaming agent. Suitable foaming agents include, but are not limited to, liquid-type sulfonates such as sodium methyl 2-sulfolaurate, disodium 2-sulfolaurate, sodium alkylbenzene sulfonate (linear), calcium alkylbenzene sulfonate (branched), amine alkylbenzene sulfonate (branched) and amine alkyl aryl sulfonate blend; liquid sulfonic acids such as alkylbenzene sulfonic acid (branched) and alkylbenzene sulfonic acid (linear); liquid alkyl ether sulfates such as ammonium ether sulfate and sodium ether sulfate; liquid olean sulfonates such as sodium alpha olefin sulfonate; liquid amphoterics such as cocoamidopropyl betaine; liquid alkyl sulfates such as ammonium lauryl sulfate, sodium lauryl sulfate and DEA lauryl sulfate; liquid betaines such as cocamidopropyl betaine; liquid sarcosinates such as sodium lauroyl sarcosinate, sulfosuccinates liquid, disodium laureth sulfosuccinate, sodium lauryl sulfoacetate; and liquid alkyl polyglycosides such as short chain alkyl polyglycosides. For example, but not by way of limitation, an application hose may be placed within the sewer from one manhole, or access point, to another. Compressed air may be injected into the stream of mixed solution as it is being pumped, in order to create a foam. The foam may then be ejected under pressure, filling the sewer as the hose is retrieved.

In preferred embodiments of the invention, paraquat may be used with a cationic, neutral or non-ionic foaming agent. Paraquat is typically not compatible with anionic foaming agents. However, the use of moderately ionic (i.e., 50% or less of the foaming agent components are anionic and the remainder are neutral or cationic) is possible, provided that application takes place promptly after mixing paraquat and foaming agent in solution.

The objective of foam application techniques is generally to fill a pipe with foam as completely as possible as the application hose is being retrieved. The filling capability may be optimized by altering the rate at which the application hose is retrieved. In order to fill a pipe with foam, the application hose may be retrieved at a rate (feet per minute) equal to the gallons of foam generated per minute divided by the volume (gallons per foot of length) of pipe.

As a first specific, nonlimiting example of the invention, typical foaming compounds are associated with an expansion ratio of 20 to 1 when applied via standard sewer foaming equipment. This equipment is normally run at a rate which utilizes 4.5 gallons of solution per minute, which therefore produces 90 gallons of foam per minute (4.5 gallons×20). The volume of an 8 inch diameter pipe is approximately 2.6 gallons per foot of length. At an application rate of 90 gallons of foam per minute in an 8 inch diameter pipe, the hose should be retrieved at a rate of approximately 35 feet per minute (90 gallons/minute÷2.6 gallons per foot=35 feet per minute).

As a second specific nonlimiting example, if a foaming compound provides a lower expansion ratio, e.g., 15 to 1, and the foam application equipment is pumping solution at a lower rate, e.g., 3.5 gallons per minute, then the application hose ejects approximately 53 gallons of foam per minute (3.5×15=53). If the pipe to be treated is 10" in diameter, the volume of said pipe is approximately 4 gallons per foot. The hose retrieval rate in this example would be approximately 13 feet per minute (53 gallons per minute÷4 gallons per foot=13.25).

The flow in large diameter pipes (e.g., 15" and greater) will often overpower the foam such that it cannot fill the pipe and remain in place. This job condition may be handled by applying a 3" to 4" coating of foam along the entire inside circumference of the pipe. The volume of foam required to coat a pipe may be calculated by determining the volume of the pipe to be treated (per foot), and subtracting from that the volume of a pipe 6 to 8 inches smaller in diameter (per foot).

Figure 2:
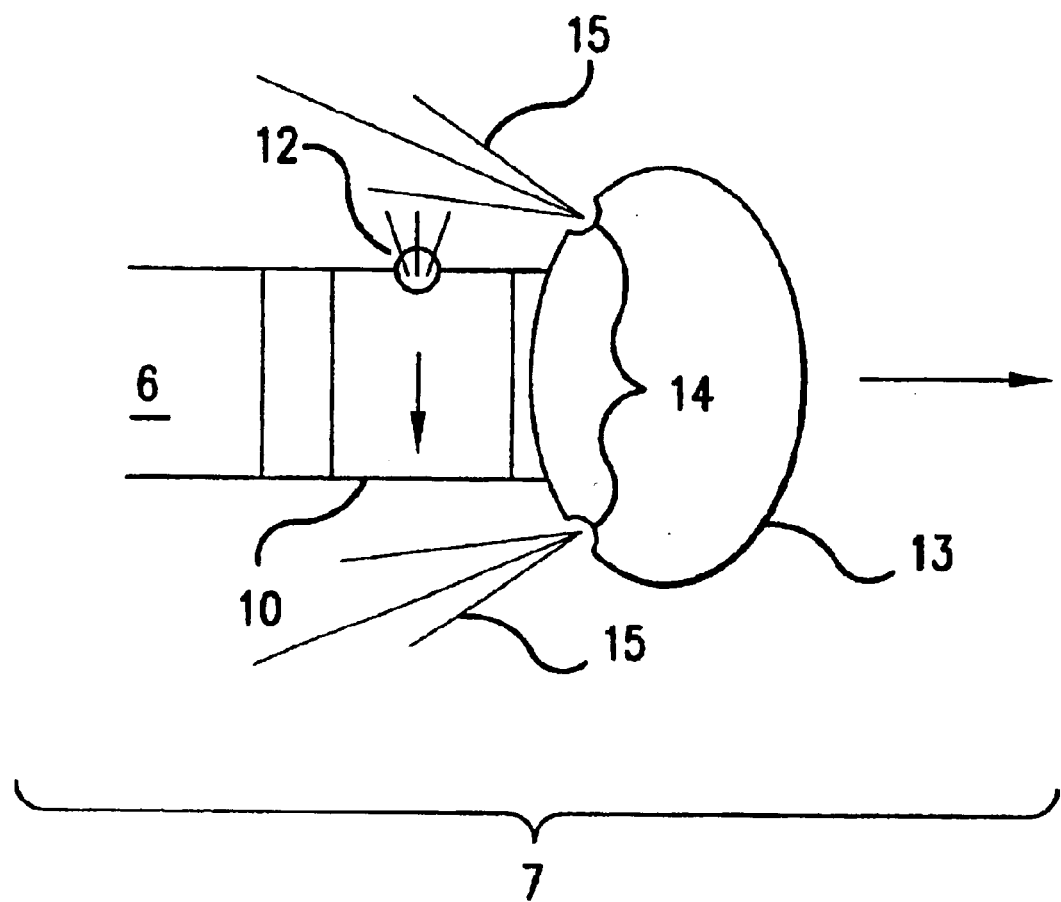
FIG. 2. Expanded view of the jet nozzle referred to in FIG. 1. The nozzle is located at the free end of the high pressure hydraulic sewer cleaning hose (6). It is comprised of a center body (10) that spins in a direction perpendicular to the direction in which the hose is traveling. The center body has one or more side water port (11) that ejects water (12) in a direction that is approximately perpendicular to the direction that the hose is traveling. At the distal end of the nozzle is a stationary portion (13) having multiple rearward facing ports (14) which eject water (15) so as to propel the nozzle and hose forward, in the direction of the large arrow.
Figure 3:
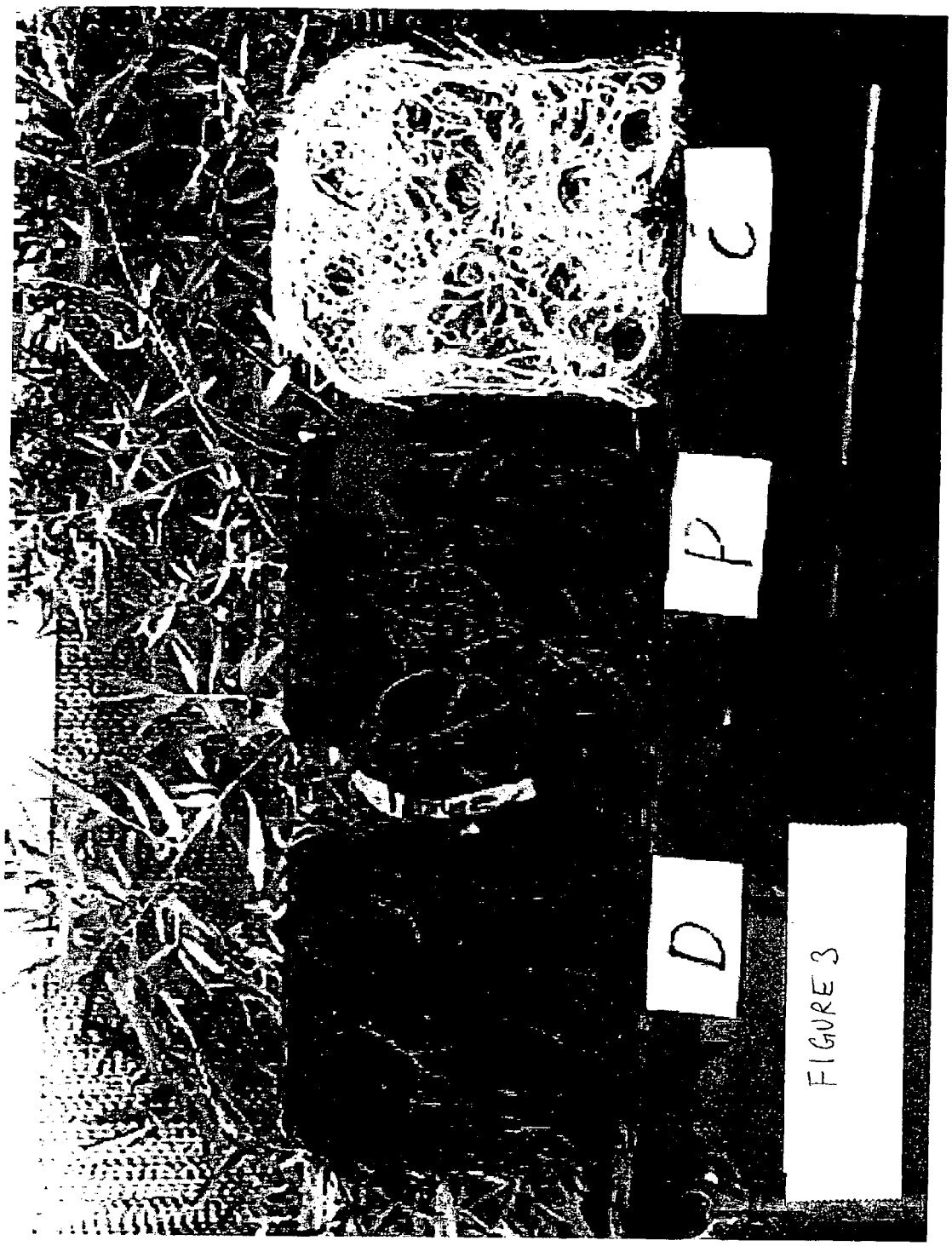
FIG. 3 shows the effect of paraquat on root growth in comparison to diquat and the untreated control. (D=diquat; P=paraquat; C=control).
Figure 4:
FIG. 4 demonstrates the effect of diquat in comparison to Rootex, a rooting hormone. (D=diquat; R=Rootex).

In a second set of nonlimiting embodiments, paraquat solution may be applied to exposed roots as a spray, for example as applied by a hydraulic sewer cleaning machine (henceforth referred to as a "Sewer Jet") as depicted in FIGS. 1 and 2 or other spraying device. A Sewer Jet should be operated using parameters (e.g. pressures and retrieval rates) recommended by the manufacturer. It is advisable to recirculate water within the jet truck in order to ensure an even distribution of paraquat. Several brands and styles of sewer jetting equipment are available, including but not limited to Aquatech, Vac-Con, Vactor, Myers, Clean Earth Machine, and SRECO.

It may be preferable to mix paraquat into an ancillary tank, rather than the primary water tank of the Sewer Jet (see FIG. 1). In this way, fresh water from the primary water tank is used to jet the hose up the pipe, and the paraquat solution in the secondary tank is pumped as the hose is retrieved, by switching off the fresh water tank and switching on the solution tank. Heavy roots and other obstacles may impede the progress of the hose when jetting up a line. This can cause wasteful over-application of chemical in those areas. The applicator should be cautioned to ensure that the Sewer Jet hose has been purged of fresh water and is dispensing paraquat solution before beginning to retrieve the hose.

In preferred embodiments of the invention, a Sewer Jet is equipped with a spinning nozzle, which provides better coverage of the spray solution within the pipe. Typical Sewer Jet nozzles are rearward facing and propel the Sewer Jet hose down a pipe line. The spinning nozzle variant has a side port that jets water in a direction approximately perpendicular to the pipe wall. The jetting action from this side port causes the nozzle body to spin, thereby causing the direction of the spray to rotate, thereby widely distributing sprayed liquid over the inner surface of the pipe. In further preferred embodiments of the invention, a Sewer Jet is equipped with a spray port designed to fog or atomize the spray solution, which minimizes droplet size, and reduces run-off. Fogging sewer jet nozzles and spinning sewer jet nozzles are common stock items for most sewer jet manufacturers.

In view of the toxicity of paraquat, it is imperative that the applicator wear a respirator and additional safety equipment to protect, among other things, from pulmonary and transcutaneous exposure. The use of hot water or steam in conjunction with application of parauat may be dangerous.

EXAMPLE

Destruction of Root Tissue by Paraquat

Materials and Methods

Individual branch cuttings of black willow (*Salix nigra*) were collected and grown in containers according to methods described in Groninger and Bohanek 2000, J. of Plant Growth Regulation 19:453–456. The cuttings were rooted in 262 ml tubes containing a 1:1 mixture of peat moss and white washed play sand. Tubes were perforated with a 2 $cm^2$ hole in the bottom and four 1.4 $cm^2$ holes on the side, 2 cm from the bottom of the tube. Cuttings were grown under greenhouse conditions in racks containing 12 tubes each with one cutting per tube. To facilitate root growth outside of the tube, the racks were placed in aluminum pans and positioned so that the base of each tube was suspended in dilute nutrient solution. Water was added as needed and a 20-20-20-NPK fertilizer was provided at a rate of 0.04 g/cutting per week into the pan. Root growth was further facilitated by maintaining the root zone in darkness by covering gaps between the edge of the rack and the pan with aluminum foil. When cuttings had been growing for approximately four months, intermingling exposed roots from adjacent cuttings were separated from one another and fine roots were allowed to regrow. Treatment were initiated when shoots averaged 0.8 meters in height with healthy foliage. At the time of treatment, each cutting produced profuse growth of roots 0.3 cm in diameter or less.

Roots of the cuttings were exposed to paraquat, diquat, Rootex, a rooting hormone, and a control. Paraquat (Gramoxone Max®, Syngenta, containing 43.8% paraquat) was applied to roots cuttings at two rates, 2.0 and 4.0 ml/L. Diquat (Reward®, Syngenta, containing 37.3% diquat) was applied at 4.0 ml/L. Each treatment of the four treatments were applied in 1.0 L water solution with a 2% alkyl polyglycoside-based foaming agent, AU-340 (Adjuvants Unlimited, Tulsa, Okla.) using a foam generator to simulate a standard application of chemicals in controlling tree roots in sewer lines. Roots were placed in contact with foam solution for 20 minutes. Dense root growth at the time of treatment prevented the movement of foam into the tube containing the cutting. Upon removal of foam solution, cuttings and their exposed roots were returned to pretreatment nutrient conditions with residual foam permitted to maintain contact with exposed roots.

Evaluation of roots was conducted twenty-five days following treatment. Roots were visually inspected, harvested, separated into living and dead groups, dried and weighed for dry mass determination.

Results

Untreated controls displayed abundant root growth and no evidence of dead roots (FIG. 3). Rootex-treated controls exhibited abundant root growth (FIG. 4). No living roots were observed in the diquat or paraquat treated roots (FIG. 3).

Table 1 demonstrates that there is no root growth in diquat or paraquat treated roots.

TABLE 1

Dry Weight of Roots Twenty-five Days following Treatment
(Each value represents the average of 24 willows cuttings.)

| Treatment | Live Roots (g/willow cutting) | Dead Roots (g/willow cutting) |
|---|---|---|
| Control | 5.7 | 0 |
| Diquat* (4.0 ml/L) | 0 | 0.9 |
| Paraquat** (2.0 ml/L) | 0 | 0.7 |
| Paraquat** (4.0 ml/L) | 0 | 2.2 |

*dilution of a 37.3% diquat stock
**dilution of a 43.8% paraquat stock

These results show that paraquat is effective for controlling the growth of tree roots, and may be more toxic to roots than diquat.

Various publications are cited herein, the contents of which are hereby incorporated by reference in their entireties.

What is claimed is:

1. A method of controlling the growth of an exposed root, comprising applying, to the root, an effective amount of paraquat ion, wherein the application of the paraquat does not damage plant tissue above the root.

2. The method of claim 1, wherein the paraquat ion is applied to the exposed root as a foam.

3. The method of claim 1, wherein the paraquat ion is applied to the exposed root as a spray.

4. The method of claim 3, wherein the spray comprises paraquat ion and hot water.

5. The method of claim 3, wherein the spray is applied to the root by a hydraulic sewer cleaning machine.

6. The method of claim 4, wherein the spray is applied to the root by a hydraulic sewer cleaning machine.

7. A method of controlling the growth of an exposed root, comprising applying, to the root, an effective amount of paraquat ion and a second herbicidal agent selected from the group consisting of diquat, methyldithiocarbamate sodium and dichlorobenzonitrile.

8. The method of claim 7, wherein the paraquat ion and second herbicidal agent are applied to the exposed root as a foam.

9. The method of claim 7, wherein the paraquat ion and second herbicidal agent are applied to the exposed root as a spray.

10. The method of claim 9, wherein the spray comprises paraquat ion, a second herbicidal agent and hot water.

11. The method of claim 9, wherein the spray is applied to the root by a hydraulic sewer cleaning machine.

12. The method of claim 10, wherein the spray is applied to the root by a hydraulic sewer cleaning machine.

13. A method of treating a conduit to effectively kill roots obstructing the conduit, comprising exposing the roots in the conduit to a solution comprising an effective concentration of paraquat ion.

14. The method of claim 13, wherein the paraquat ion is applied to the roots as a foam.

15. The method of claim 13, wherein the paraquat ion is applied to the roots as a spray.

16. The method of claim 15, wherein the spray comprises paraquat ion and hot water.

17. A method of treating a conduit to effectively kill roots obstructing the conduit, comprising exposing the roots in the conduit to a solution comprising effective concentrations of paraquat ion and diquat ion.

18. The method of claim 17, wherein the solution is applied to the roots as a foam.

19. The method of claim 17, wherein the solution is applied to the roots as a spray.

20. A composition comprising paraquat and a foam-generating agent selected from the group consisting of sulfonate (linear), calcium alkylbenzene sulfonate (branched), amine alkylbenzene sulfonate (branched), amine alkyl aryl sulfonate blend, a liquid sulfonic acid, alkylbenzene sulfonic acid (branched), alkylbenzene sulfonic acid (linear), a liquid alkyl ether sulfate, ammonium ether sulfate, sodium ether sulfate, a liquid olean sulfonate, sodium alpha olefin sulfonate, a liquid amphoteric, cocoamidopropy betaine, a liquid alkyl sulfate, ammonium lauryl sulfate, sodium lauryl sulfate, DEA lauryl sulfate, a liquid betaine, cocamidopropyl betaine, a liquid sarcosinate, sodium lauroyl sarcosinate, sulfosuccinates liquid, disodium laureth sulfosuccinate, sodium lauryl sulfoacetate, a liquid alkyl polyglycoside, and a short chain alkyl polyglycoside.

21. A foam for application in conduit comprising an effective amount of paraquat, prepared by blowing compressed air through a solution comprising paraquat and a foam generating agent.

* * * * *